(12) United States Patent
Kim et al.

(10) Patent No.: US 6,501,823 B1
(45) Date of Patent: Dec. 31, 2002

(54) METHOD OF RECONSTRUCTING A TOMOGRAM OF AN X-RAY APPARATUS

(75) Inventors: Hyeong-Cheol Kim, Seongnam (KR); Won Choi, Suwon (KR); Jae-Hyun Jung, Anyang (KR); Yong-Won Kim, Suwon (KR); Hyoung-Jo Jeon, Yongin (KR); Seung-Hwan Choi, Seoul (KR); Hyun-Kwon Jung, Kwangmyong (KR); Kwang-Jun Yoon, Seoul (KR); Jun-Bo Kim, Seoul (KR); Kyoung-Mu Lee, Seoul (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 10/053,875

(22) Filed: Jan. 24, 2002

(30) Foreign Application Priority Data

Jul. 6, 2001 (KR) .......................................... 01-40219

(51) Int. Cl.⁷ .............................................. G01N 23/00
(52) U.S. Cl. ............................................ 378/22; 378/25
(58) Field of Search ................................ 378/23, 98.11, 378/98.12, 22, 25

(56) References Cited

U.S. PATENT DOCUMENTS

| | | | | |
|---|---|---|---|---|
| 6,292,527 B1 | * | 9/2001 | Guendel ....................... | 378/15 |
| 6,298,111 B1 | * | 10/2001 | Ozaki ............................ | 378/8 |
| 6,418,186 B1 | * | 7/2002 | Kawai et al. .................. | 378/19 |
| 6,426,987 B2 | * | 7/2002 | Nakamura et al. ............. | 378/4 |

* cited by examiner

Primary Examiner—Robert H. Kim
Assistant Examiner—Irakli Kiknadze
(74) Attorney, Agent, or Firm—Staas & Halsey LLP (57) ABSTRACT

A method of reconstructing a tomogram of an X-ray apparatus. The tomogram reconstructing method includes obtaining model information and a transmission image of a subject. A tomogram is reconstructed from the transmission image using the model information. The reconstructed tomogram obtained is then displayed.

7 Claims, 9 Drawing Sheets

METHOD OF RECONSTRUCTING A TOMOGRAM OF AN X-RAY APPARATUS

CROSS REFERENCE TO RELATED APPLICATIONS

This application claims the benefit of Korean Application No. 2001-40219 filed Jul. 6, 2001, in the Korean Patent Office, the disclosure of which is incorporated herein by reference.

BACKGROUND OF THE INVENTION

1. Field of the Invention

The present invention relates generally to X-ray apparatuses, and more particularly to a method of reconstructing a-tomogram of an X-ray apparatus to obtain a three-dimensional image from X-ray images.

2. Description of the Related Art

Figure 1:
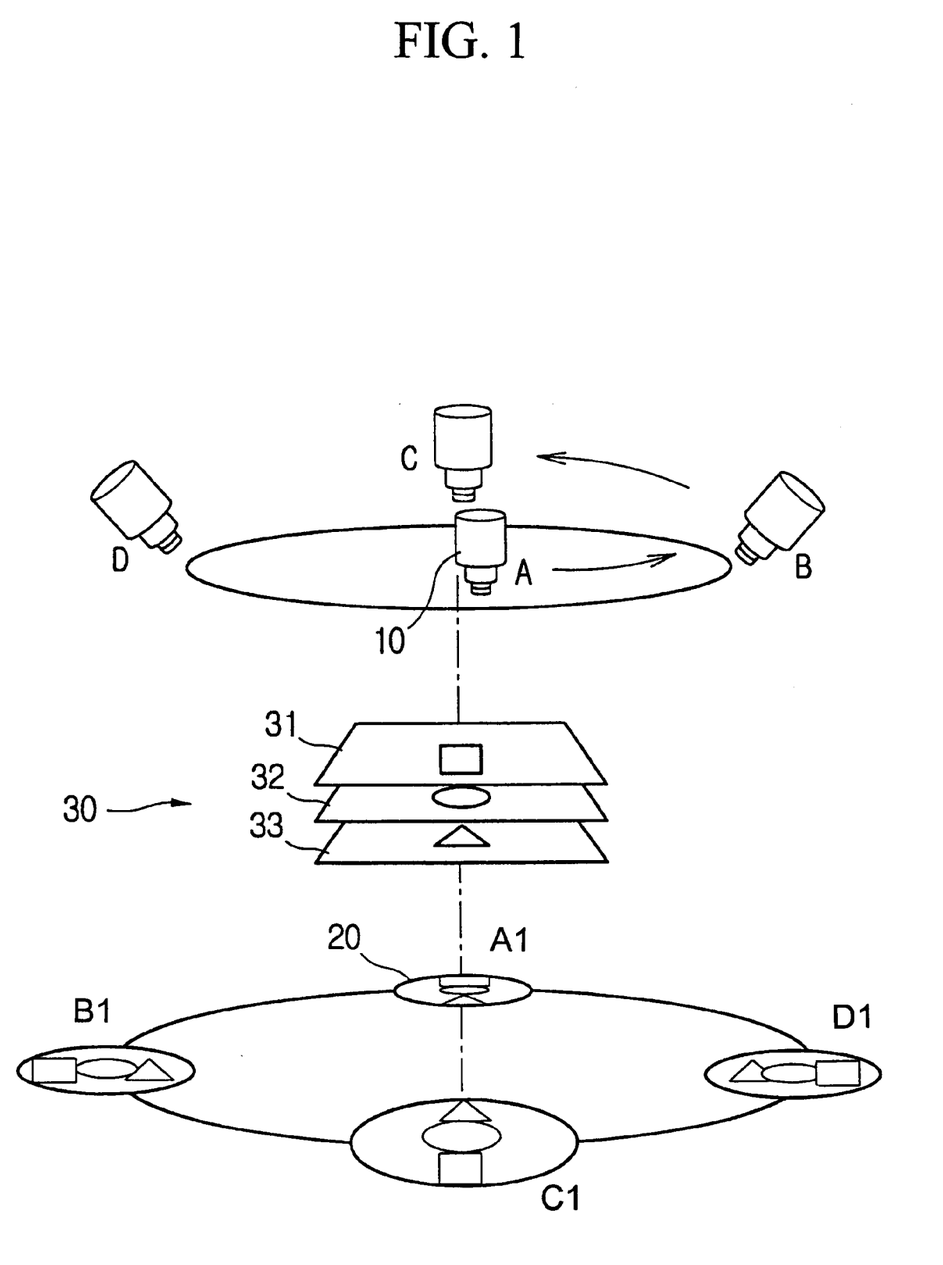
FIG. 1 is a schematic diagram showing the photographing operation of a conventional X-ray apparatus.

FIG. 1 is a schematic diagram showing a photographing operation of a conventional X-ray apparatus.

Figure 2:
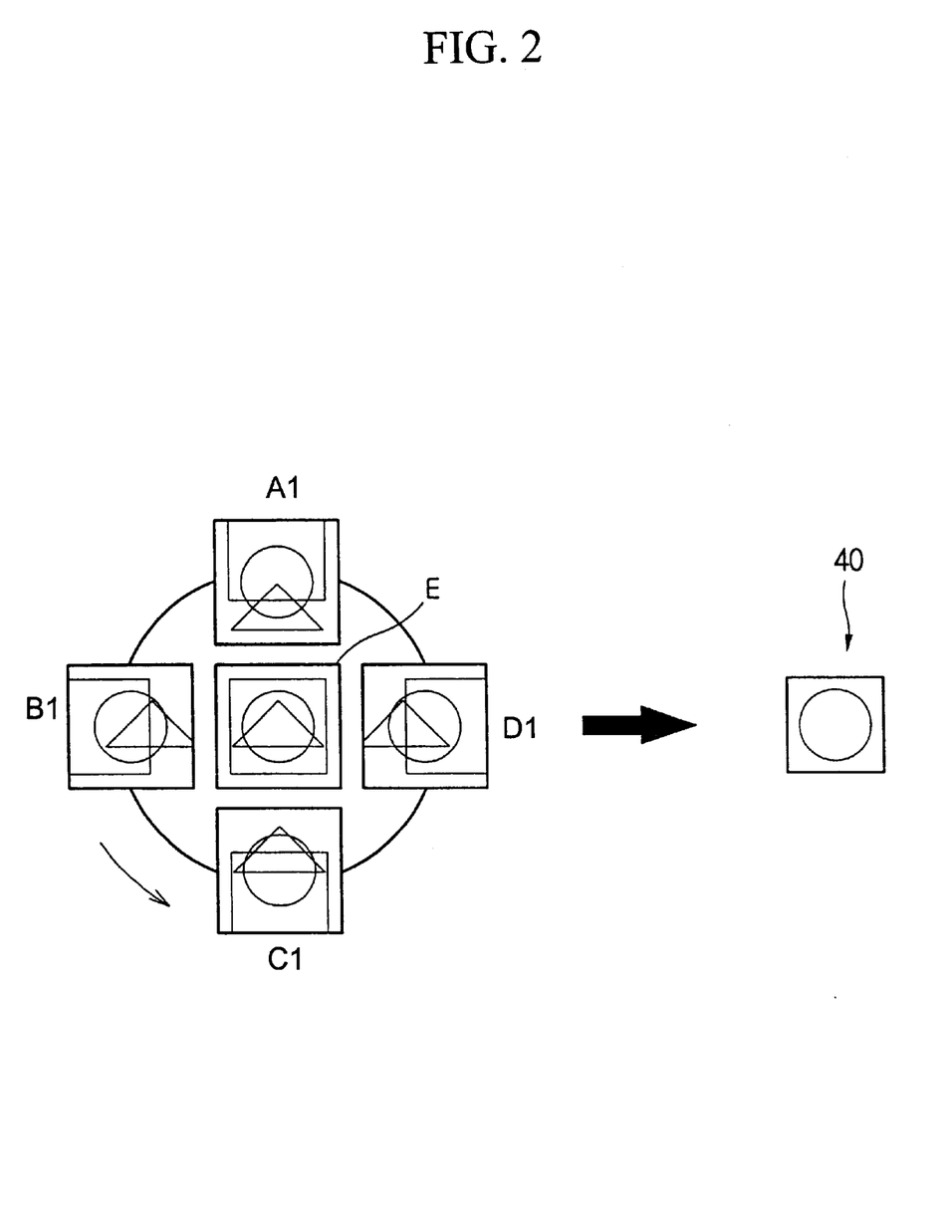
FIG. 2 is a view showing an image processing process.

Referring to FIG. 1, while being rotated around a first circular orbit, an X-ray irradiator 10 irradiates X-rays to a subject 30 at positions A, B, C and D on a first circular orbit. At this time, an X-ray detector 20 is rotated in conjunction with the X-ray irradiator 10 around a second circular orbit having the same central axis as the first circular orbit. Accordingly, the X-ray detector 20 detects X-rays which have been transmitted through the subject 30 at positions A1, B1, C1 and D1 on the second circular orbit. Images detected by the X-ray detector 20 at the positions A1, B1, C1 and D1 are illustrated in FIG. 2.

Thereafter, the conventional X-ray apparatus constructs a target image 40 of a cross section, that is, a desired focal plane 32, by overlapping a vertical transmission image E and a plurality of slant transmission images obtained by detecting the X-rays which have been transmitted through the subject 30 at positions A1, B1, C1 and D1.

However, the conventional X-ray apparatus of FIG. 1 is disadvantageous in that a long period of time is required to obtain a tomogram, and the precision of the apparatus deteriorates because images are obtained while an X-ray irradiator and an X-ray detector are moved in conjunction with each other to obtain the tomogram from these images.

SUMMARY OF THE INVENTION

The present invention has been made in view of the above problem, and it is an object of the present invention to provide a method of reconstructing a tomogram of an X-ray apparatus, which improves precision and reduces a required period of time to obtain a desired tomogram from a subject.

Additional objects and advantages of the invention will be set forth in part in the description which follows, and, in part, will be obvious from the description, or may be learned by practice of the invention.

To accomplish the above and other objects of the invention, the present invention provides a method of reconstructing a tomogram of an X-ray apparatus, obtaining model information of a subject; obtaining a transmission image of the subject; reconstructing a tomogram based on the transmission image and the model information; and displaying the reconstructed tomogram.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Reference will now be made in detail to the present embodiments of the present invention, examples of which are illustrated in the accompanying drawings, wherein like reference numerals refer to like elements throughout.

Figure 3:
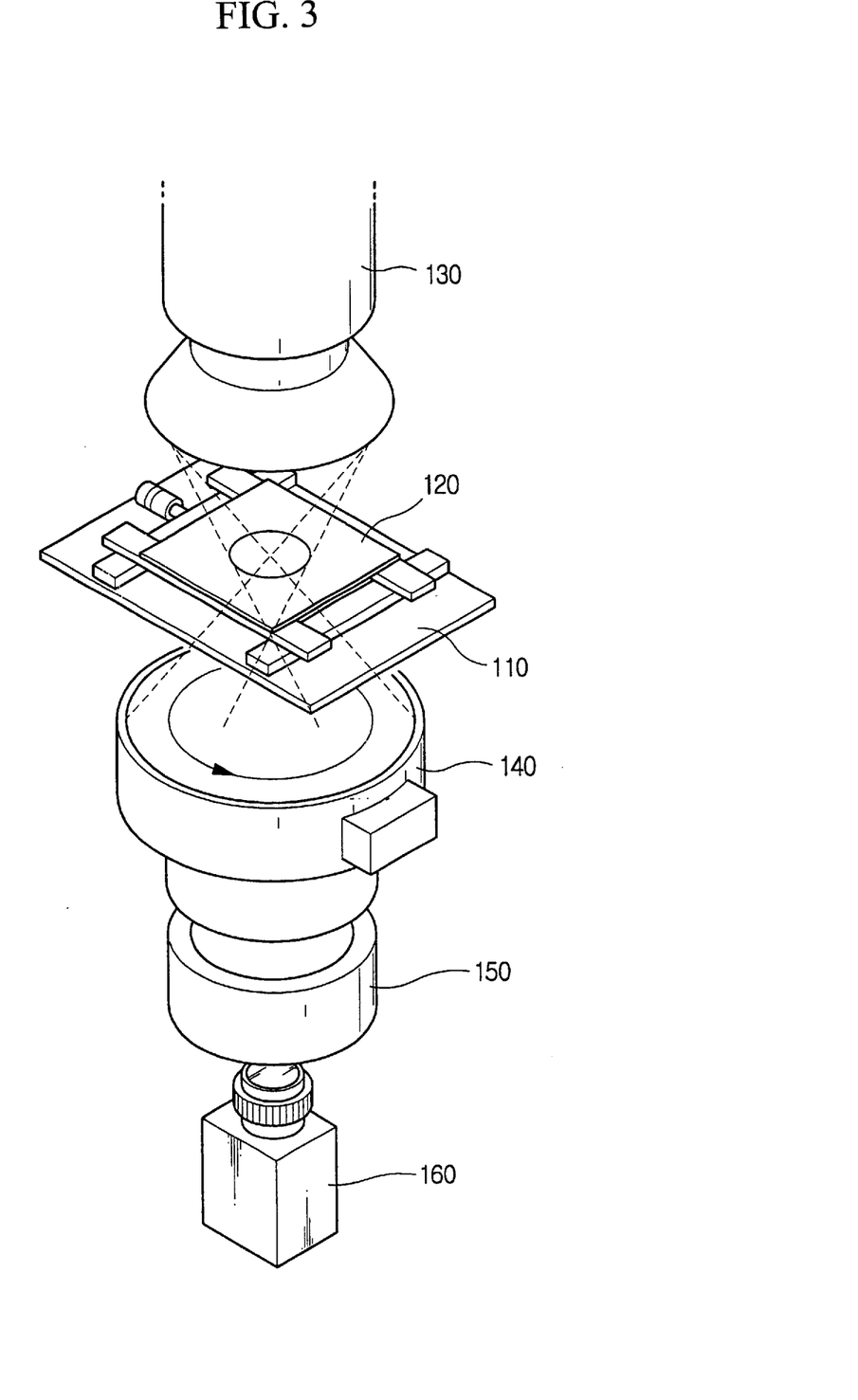
FIG. 3 is a schematic diagram showing the structure of an X-ray apparatus in accordance with the present invention.

FIG. 3 is a schematic diagram showing the structure of the X-ray apparatus in accordance with the present invention. Referring to FIG. 3, the X-ray apparatus of the present invention comprises a loading table 110 which supports a subject 120, an X-ray irradiator 130 which irradiates X-rays to the subject 120 placed on the loading table 110, an image intensifier 140 which converts X-rays transmitted through the subject 120 into a visible image, an image selection unit 150 which selects a specific region from the image converted by the image intensifier 140, and a photographing unit 160 which obtains the image of the specific region selected by the image selection unit 150.

X-rays irradiated by the X-ray irradiator 130 are transmitted through the subject 120 placed on the loading table 110 and formed on a screen of the image intensifier 140 in the form of a visible image. Accordingly, the image of the selected region is obtained by the photographing unit 160.

Figure 4:
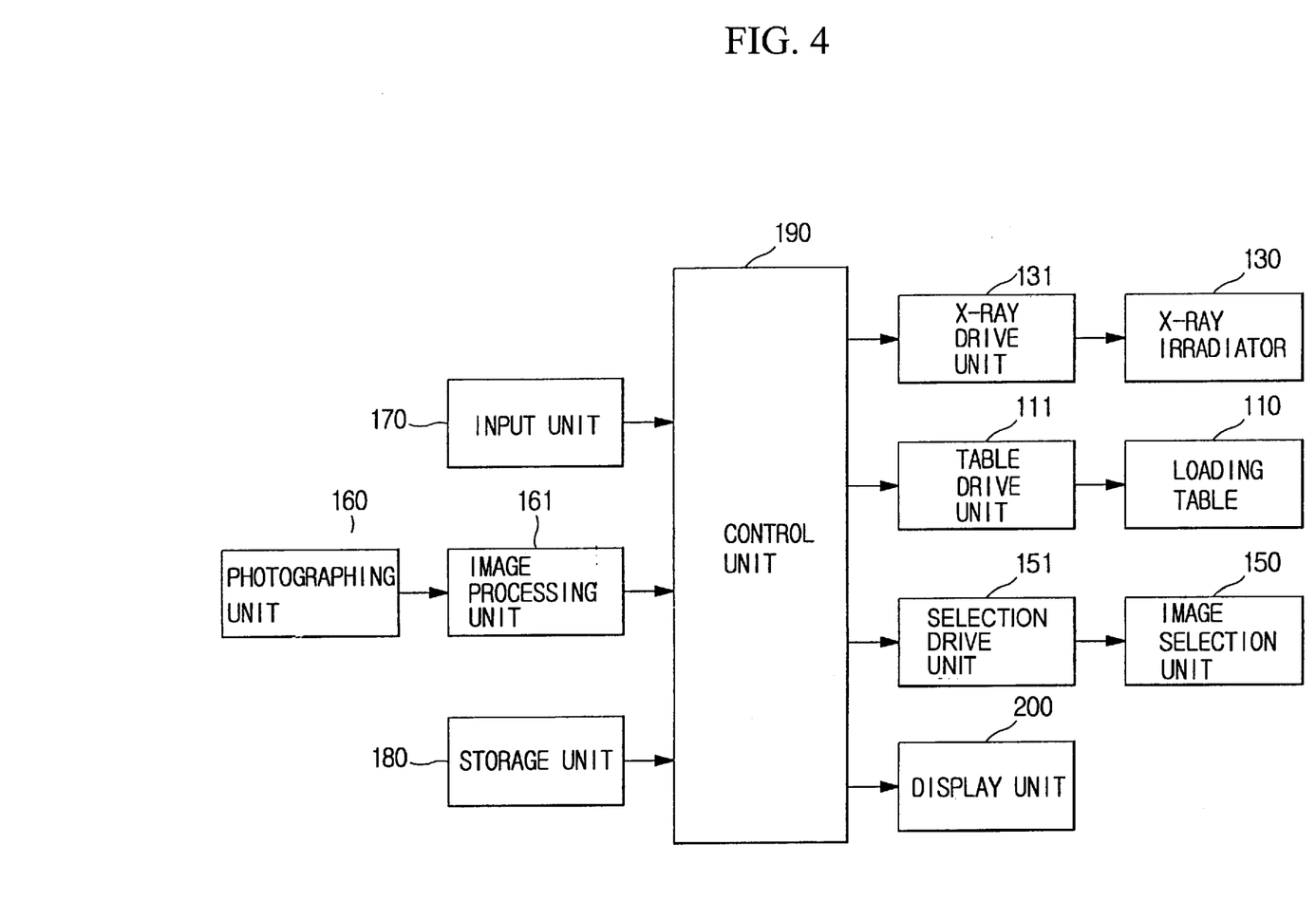
FIG. 4 is a block diagram showing the control mechanism of the X-ray apparatus of the present invention.

FIG. 4 is a block diagram showing the control mechanism of the X-ray apparatus of the present invention. Referring to FIG. 4, the control mechanism of the X-ray apparatus of the present invention comprises a control unit 190 which controls overall operation of the apparatus, an input unit 170 which receives information from a user and sends the user supplied information to the control unit 190, an X-ray drive unit 131 which drives the X-ray irradiator 130 to irradiate X-rays to the subject 120, a table drive unit 111 which drives the loading table 110 which supports the subject 120, a selection drive unit 151 which drives the image selection unit 150 to select the specific region of the image formed on the image intensifier 140, the photographing unit 160 which photographs the specific region of the image selected by the image selection unit 150, and an image processing unit 161 which processes an image taken by the photographing unit 160 and sends the processed image to the control unit 190.

Preferably, the control mechanism of the X-ray apparatus further comprises a storage unit 180 which stores image data according to the control of the control unit 190 and a display unit 200 which visually displays a processed image according to the control of the control unit 190.

Figure 5:
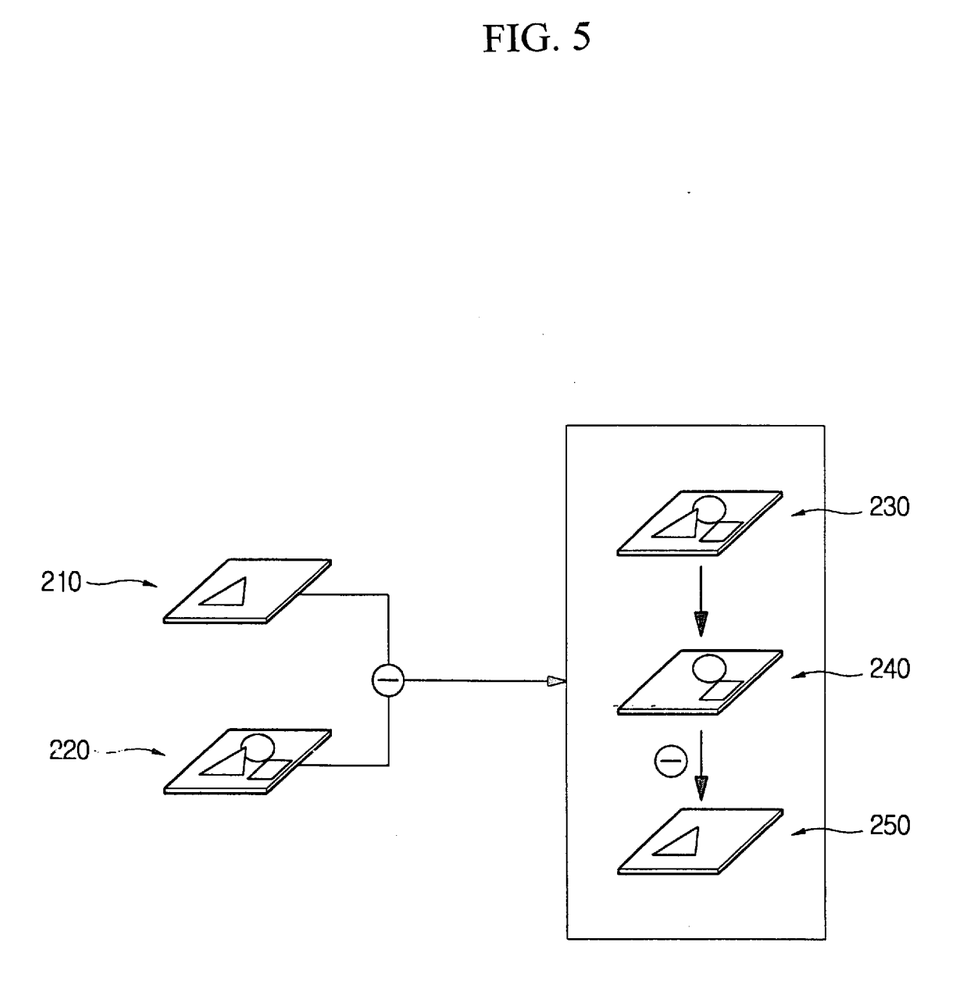
FIG. 5 is a view showing a method of reconstructing a tomogram of the X-ray apparatus of the present invention.

FIG. 5 is a view showing a method of reconstructing a tomogram of the X-ray apparatus of the present invention. Referring to FIG. 5, a user (or an examiner) obtains a tomogram 210 and a transmission image 220 of the subject 120 through a tomography apparatus. In this case, the tomogram 210 may be obtained by overlapping a plurality of images of the subject in a conventional manner.

After the tomogram 210 and the transmission image 220 are obtained, the user filters the tomogram 210 from the transmission image 220 and obtains model information 240, that is, a background image. After the model information 240 is obtained, the user obtains a general X-ray transmission image 230 of the subject 120 to be inspected and obtains a desired tomogram 250 by filtering the model information 240 from the general transmission image 230.

Figure 6:
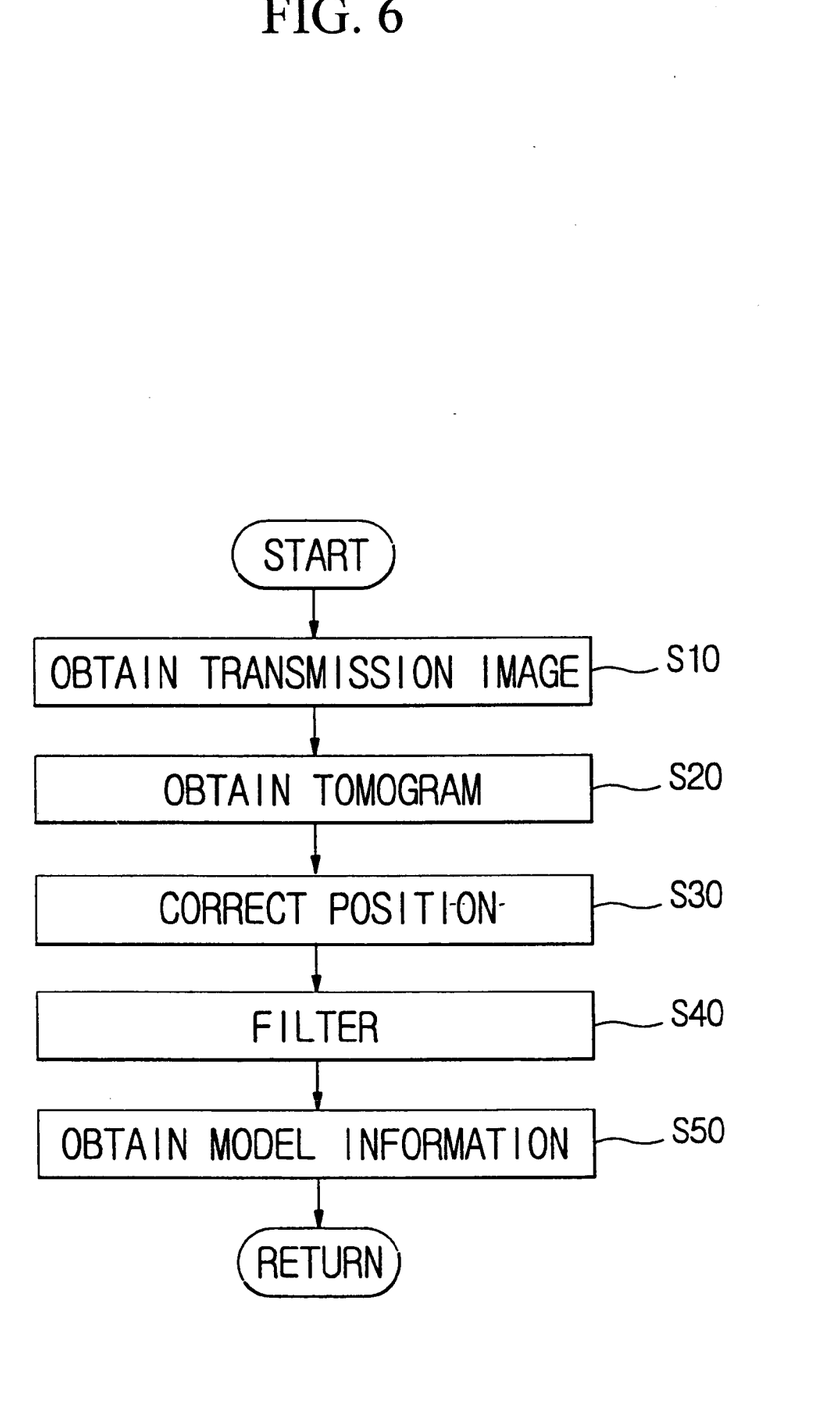
FIG. 6 is a flow chart showing obtaining of model information for use in the tomogram reconstructing method of the present invention.

FIG. 6 is a flow chart showing obtaining the model information of the tomogram reconstructing method of the present invention. Referring to FIG. 6, in order to photograph the subject 120, the control unit 190 controls the table drive unit 111 so that the loading table 110 sets a position of the subject 120 to be photographed. After the position of the subject 120 is set, the control unit 190 controls the X-ray drive unit 131 so that the X-ray irradiator 130 is operated to irradiate X-rays to the subject 120. Accordingly, the X-rays transmitted through the subject 120 are formed on the image intensifier 140. In order to photograph the image formed on the image intensifier 140, the control unit 190 controls the selection drive unit 151 to operate the image selection unit 150, and controls the photographing unit 160 to photograph the transmission image 230 formed on the image intensifier 140. The image taken by the photographing unit 160 is sent to the control unit 190 through the image processing unit 161. Accordingly, the control unit 190 obtains the transmission image and stores the transmission image in the storage unit 180 at operation S10.

After the transmission image of the subject 120 is obtained, the control unit 190 obtains a desired tomogram of the subject 120 at operation S20. In more detail, in order to obtain the tomogram of the subject 120, the control unit 190 controls the X-ray drive unit 131 so that the X-ray irradiator 130 is operated to irradiate X-rays in different directions. Additionally, the control unit 190 controls the selection drive unit 151 so that the image selection unit 150 is moved in conjunction with the X-ray irradiator 130 to select an image formed on the image intensifier 140 in the direction of the X-rays irradiated from the X-ray irradiator 130. The control unit 190 controls the photographing unit 160 to sequentially photograph the images selected by the image selection unit 150. The photographed images are sent to the control unit 190 through the image processing unit 161. The control unit 190 overlaps the images sent from the image processing unit 161. Thereafter, the tomogram of the subject 120 is obtained by overlapping, and stored in the storage unit 180.

After the transmission image and the tomogram of the subject are obtained, the control unit 190 corrects the positions of the images by correcting the errors of the coordinate axes of the transmission image and the tomogram at operation S20 so as to improve a filtering precision.

Where the correction of the positions of the images is finished, the control unit 190 removes the tomogram from the transmission image by filtering the tomogram from the transmission image at operation S40. Accordingly, the tomogram, that is, a target image, is removed from the transmission image, that is, an entire image, so the model information, that is, the background image, remains at operation S50. The control unit 190 stores the obtained model information in the storage unit 180.

As described above, after the model information of the subject is obtained, the tomogram of the subject is obtained from the transmission image using the obtained model information, as will be described in more detail below.

In order to photograph the transmission image of the subject 120, the control unit 190 controls the table drive unit 111 so that the position of the loading table 110 is changed and the position of the subject to be photographed is set. After setting the position of the subject 120, the control unit 190 controls the X-ray drive unit 131 so that the X-ray irradiator 130 is operated to irradiate X-rays to the subject 120. Accordingly, the X-rays transmitted through the subject 120 are formed on the image intensifier 140. In this case, the control unit 190 controls the selection drive unit 151 so that image selection unit 150 selects and fixes a predetermined position of the image intensifier 140, that is, the position where the transmission image is formed. Therefore, an error in the position where the transmission image is formed is considerably reduced, so the precision of the tomogram is improved.

The control unit 190 controls the photographing unit 160 to photograph the transmission image formed on the image intensifier 140 fixed and selected by the image selection unit 150. The image taken by the photographing unit 160 is sent to the control unit 190 through the image processing unit 161.

Figure 7:
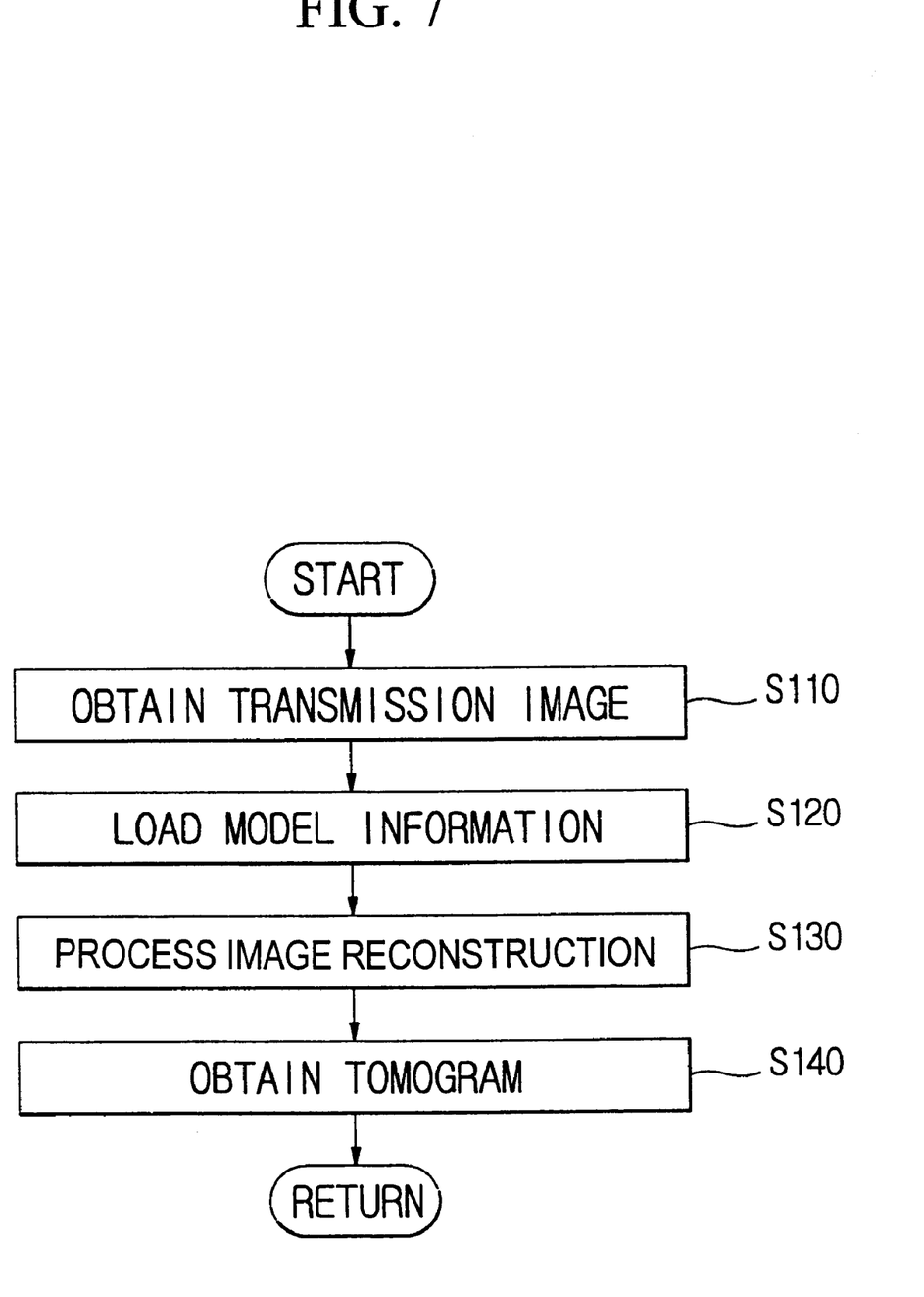
FIG. 7 is a flow chart showing the tomogram reconstructing method of the present invention.

FIG. 7 is a flow chart showing the tomogram reconstructing method of the present invention. Referring to FIG. 7, the control unit 190 obtains the transmission image and stores the obtained transmission image data in the storage unit 180 at operation S110. After obtaining the transmission image, the control unit 190 loads the model information previously stored in the storage unit 180 at operation S120. In this case, the transmission image is the entire image of the subject 120, and the model information is the background image except for the desired image of the subject 120.

The control unit 190 reconstructs the image using the transmission image and the model information so as to obtain a desired tomogram of the subject 120 at operation S130. The control unit 190 removes the model information (the background image) from the transmission image in the process of reconstructing the tomogram. Accordingly, the user obtains the desired tomogram of the subject 120 at operation S140. The display unit 200 visually displays the obtained tomogram according to the control signal of the control unit 190.

Figure 8A:
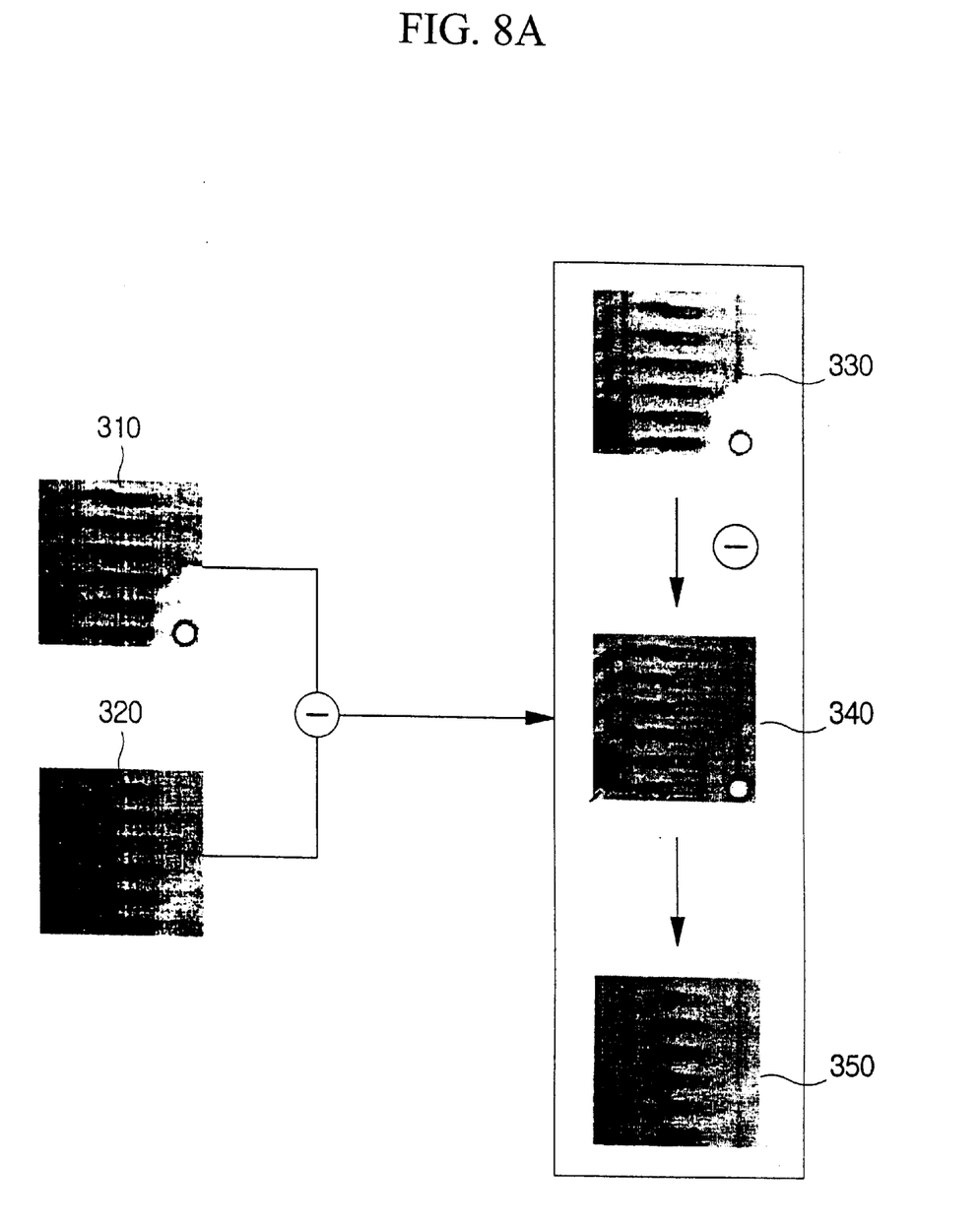
FIG. 8A is a view showing an example in which the tomogram reconstructing method of the present invention is applied to an actual subject.
Figure 8B:
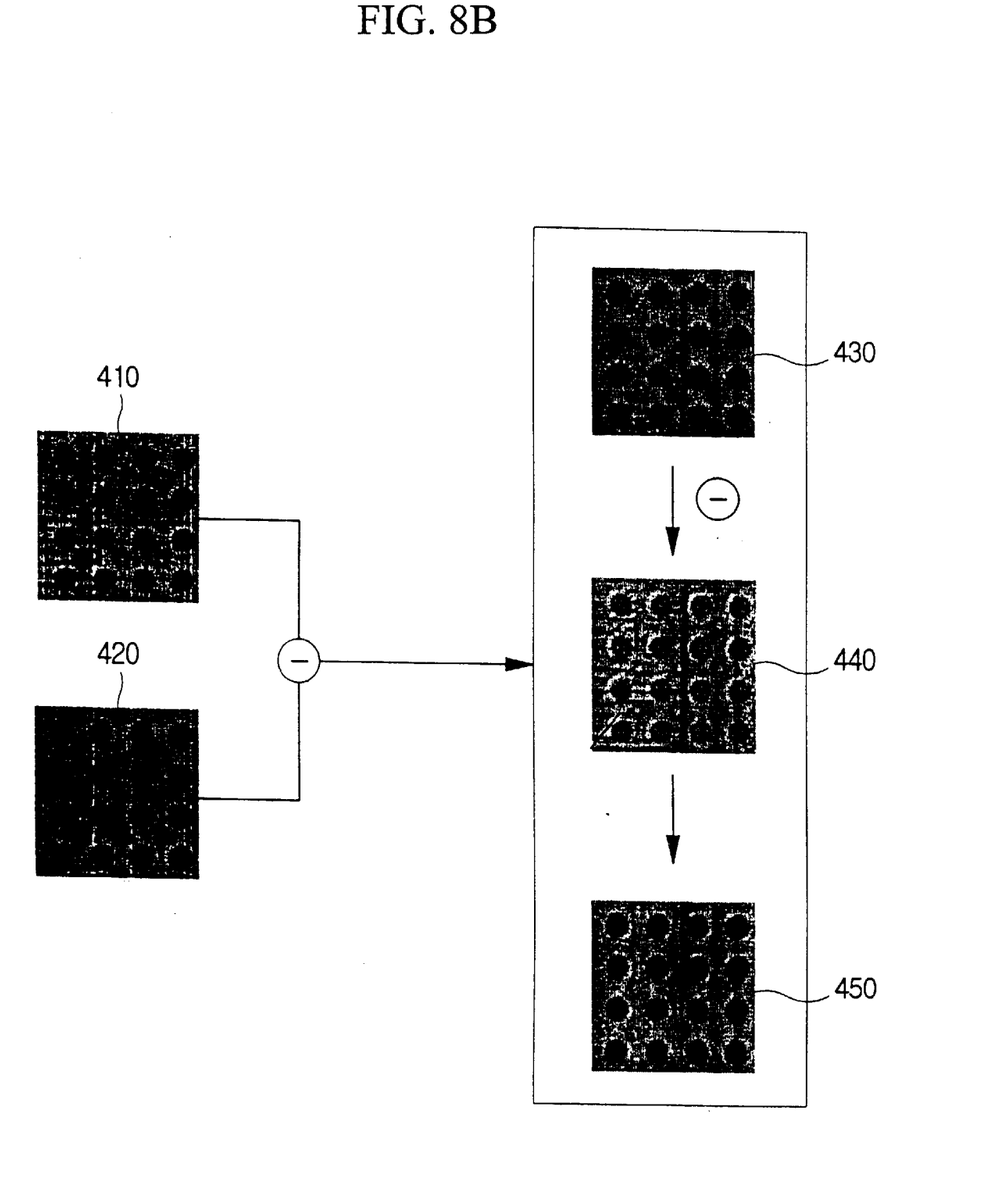
FIG. 8B is view showing another example in which the tomogram reconstructing method of the present invention is applied to another actual subject.

FIGS. 8A and 8B are views showing examples in which the tomogram reconstructing method of the present invention is applied to actual subjects. In FIG. 8A, the subject 120 is a lead. A transmission image 310 is obtained through a tomography apparatus, and a tomogram 320 of a desired focal plane is obtained. Model information, or a background image is obtained by filtering the tomogram 320 from the obtained transmission image 310. After the model information 340 is obtained, a general transmission image 330 of the subject 120 to be inspected is obtained. Finally, the tomogram 350 of a desired focal plane is obtained by filtering off the model information 340 from the general transmission image 330.

In FIG. 8A, the subject 120 is a ball grid array. A transmission image 410 is obtained through a tomography apparatus, and a tomogram 420 of a desired focal plane is obtained. Model information, or a background image 440 is obtained by filtering off the tomogram 420 from the obtained transmission image 410. After the model information 440 is obtained, a general transmission image 430 of the subject 120 to be inspected is obtained. Finally, the tomogram 450 of a desired focal plane is obtained by filtering off the model information 440 from the general transmission image 430.

As apparent from the above description, in the tomogram reconstructing method of the present invention, the model information of a subject is previously obtained and a desired tomogram is obtained by filtering off the model information from the transmission image of the subject, thereby improving not only a processing speed but also the precision of image processing for obtaining the tomogram. Additionally, the model information of the subject is previously obtained, so a desirable tomogram is obtained at a high speed even with an X-ray apparatus for photographing only transmission images.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A method of reconstructing a tomogram of an X-ray apparatus, comprising:

obtaining model information of a subject;

obtaining a transmission image of the subject;

reconstructing a tomogram from the obtained transmission image using the model information; and displaying the reconstructed tomogram.

2. The method as set forth in claim 1, wherein the obtaining of the model information comprises:

obtaining a second transmission image of the subject through tomography;

obtaining a reference tomogram of the subject through tomography;

correcting coordinate axes of the second transmission image and the reference tomogram; and filtering the reference tomogram from the second transmission image.

3. The method as set forth in claim 1, wherein the reconstructing of the tomogram comprises filtering the model information from the transmission image.

4. A method of constructing a tomogram of a subject, the method comprising:

obtaining a first transmission image of the subject;

obtaining a reference tomogram of the subject;

filtering the reference tomogram from the first transmission image to obtain a background image;

obtaining a second transmission image of the subject; and removing the background image from the second transmission image to construct the tomogram.

5. The method as set forth in claim 4, further comprising:

correcting coordinate axes of the first transmission image and the reference tomogram prior to the filtering of the reference tomogram to obtain the background image.

6. The method as set forth in claim 4, further comprising:

storing the background image prior to obtaining the second transmission image.

7. The method as set forth in claim 4, wherein:

the obtaining of the first transmission image and the reference tomogram are performed by a tomogram apparatus and the obtaining of the second transmission image is performed with a general X-ray apparatus.

\* \* \* \* \*